US008498377B2

(12) United States Patent
Fadler et al.

(10) Patent No.: US 8,498,377 B2
(45) Date of Patent: Jul. 30, 2013

(54) IMAGING APPARATUS

(75) Inventors: Franz Fadler, Hetzles (DE); Robert Fasbender, Erlangen (DE); Armin Fürst, Erlangen (DE); Burkhard Groh, Nürnberg (DE); Reiner Franz Schulz, Dormitz (DE); Kaiss Shanneik, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 278 days.

(21) Appl. No.: 12/958,149

(22) Filed: Dec. 1, 2010

(65) Prior Publication Data

US 2011/0135051 A1 Jun. 9, 2011

(30) Foreign Application Priority Data

Dec. 4, 2009 (DE) .......................... 10 2009 057 066

(51) Int. Cl.
*A61N 5/10* (2006.01)
(52) U.S. Cl.
USPC .............................................. 378/65; 378/62
(58) Field of Classification Search
USPC ...................................................... 378/62, 65
See application file for complete search history.

(56) References Cited

U.S. PATENT DOCUMENTS

| 5,751,781 | A | 5/1998 | Brown et al. |
| 6,654,440 | B1 | 11/2003 | Hsieh |
| 7,003,072 | B2 | 2/2006 | Cohen et al. |
| 2003/0235267 | A1 | 12/2003 | Hsieh et al. |

OTHER PUBLICATIONS

German Office Action dated Jul. 20, 2010 for corresponding German Patent Application No. DE 10 2009 057 066.7 with English translation.
Zhang, T. et al., "Tetrahedron beam computed tomography (TBCT): a new design of volumetric CT system", Institute of Physics and Engineering in Medicine, 2009, pp. 3365-3378.
Bhagtani, R. et al., "Simulated scatter performance of an inverse-geometry dedicated breast CT system", Med Phys. 36 (3), Mar. 2009; pp. 788 to 796.

*Primary Examiner* — Courtney Thomas
(74) *Attorney, Agent, or Firm* — Lempia Summerfield Katz LLC

(57) ABSTRACT

An imaging apparatus for irradiating an object includes a source arrangement, from which x-rays from different positions that form an at least one-dimensional structure may be emitted. The imaging apparatus also includes a detector arrangement for detecting the x-rays. An object is positioned between the source arrangement and the detector arrangement so that, with the detector arrangement, the x-rays attenuated by the object are recorded. The imaging apparatus also includes an evaluation apparatus for evaluating the signals recorded by the detector arrangement. A region of the detector arrangement is assigned to different positions of the structure, from which x-rays are directed at the region in partial irradiations. The region is aligned relative to the structure, such that the partial irradiations that are produced from the different positions of the structure with a region of the detector develop a radiation geometry that irradiates the object in a planar fashion.

26 Claims, 10 Drawing Sheets

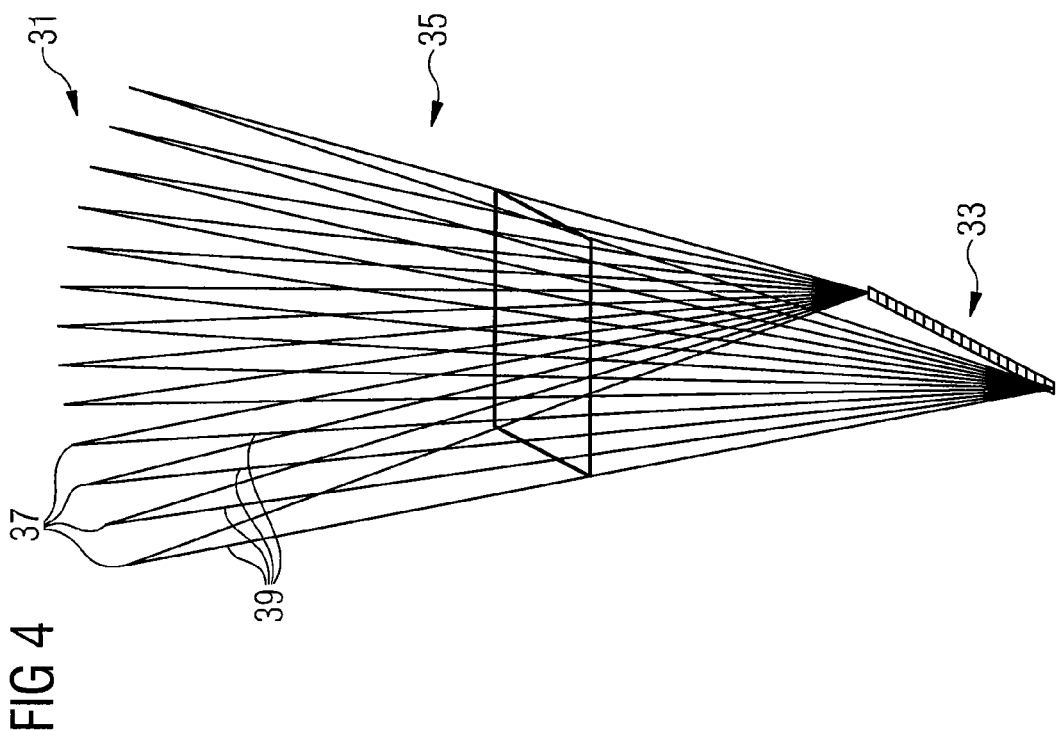
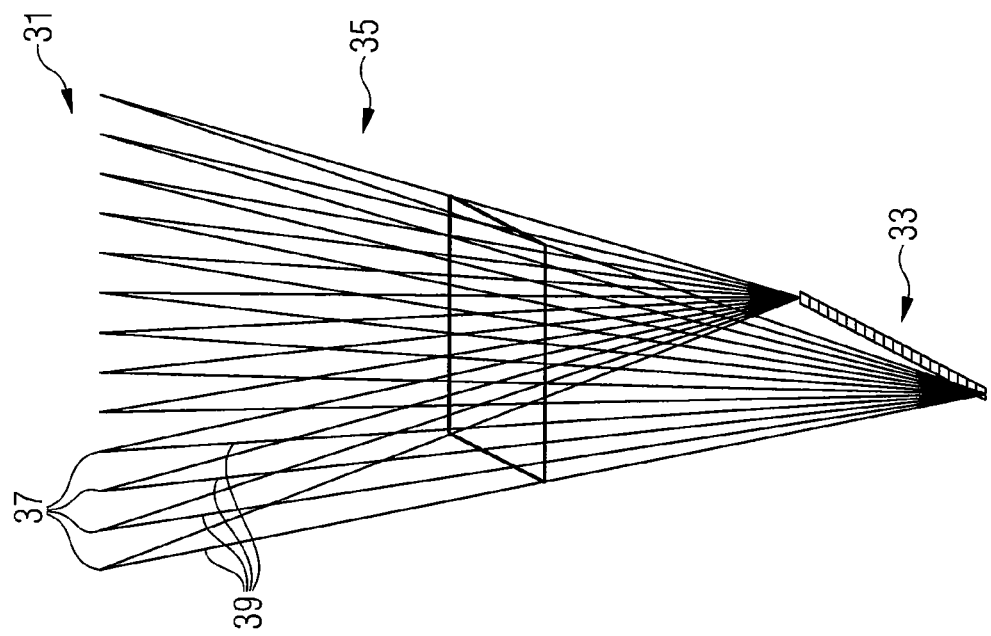

IMAGING APPARATUS

This application claims the benefit of DE 10 2009 057 066.7, filed Dec. 4, 2009, which is hereby incorporated by reference.

BACKGROUND

The present embodiments relate to an imaging apparatus for irradiating an object using x-rays.

Within the scope of medical imaging, the production of images of a patient with the aid of x-rays is an established method. A conical beam originating from an x-ray source may be directed at a planar detector. An image of the anatomy of the patient may be produced from the attenuation of the x-rays penetrating the patient.

Methods such as cone beam computed tomography, in which a plurality of planar x-ray irradiations that are rotated relative to one another are evaluated and calculated to form a three-dimensional image of the patient, are likewise known.

Radiation therapy devices that include a kV x-ray apparatus exist in order to be able to monitor the position of the patient and the tumor to be irradiated before or during a planned irradiation session. Due to the space requirement of the x-ray apparatus, the x-ray apparatus may not easily be arranged in an ideal position in the radiation therapy device. Radiation therapy devices having a kV x-ray apparatus that is arranged at right angles to the therapy beam are known, for example.

Another possibility of monitoring the position of the patient is the use of the MV therapy beam that penetrates the patient. The higher energy of the x-ray spectrum nevertheless causes a poorer image quality. In addition, during the irradiation using appropriate screening, the therapy beam is restricted to the target volume, which gives rise to a limited field of vision.

U.S. Pat. No. 7,003,072 B2 discloses a method, in which a target object is irradiated from different directions with a planar fan-shaped x-ray beam.

SUMMARY AND DESCRIPTION

The present embodiments may obviate one or more of the drawbacks or limitations in the related art. For example, in one embodiment, an imaging apparatus with x-rays that enable a planar irradiation of the patient may be specified. The embodiments may be implemented as an apparatus, system, method, and/or computer program product.

An imaging apparatus for irradiating an object with x-rays includes a source arrangement, from which x-rays may be emitted from different positions, with the different positions forming an at least one-dimensional structure. The imaging apparatus includes a detector arrangement for detecting the x-rays originating from the source arrangement and emitted onto the detector arrangement. An object may be positioned to be irradiated between the source arrangement and the detector arrangement so that the x-rays attenuated through the object may be recorded with the detector arrangement. The imaging apparatus also includes an evaluation apparatus for evaluating the signals recorded by the detector arrangement. A region of the detector arrangement is assigned to different positions of the structure, from which x-rays are directed at the region in partial irradiations, in each instance. The total of the dimension of the structure and the dimension of the region may be greater than or equal to 2. The region of the detector arrangement may be spatially stationary during the directing of the x-rays from the different positions onto the region, and the region is aligned relative to the structure, such that the partial irradiations, which are produced from the different positions of the structure in the case of a spatially stationary region of the detector, develop a radiation geometry that irradiates the object in a planar fashion. Even if the region is kept spatially stationary during the direction of the x-rays, the region may be movable. For example, for detecting a first set of x-rays directed from different positions onto the region, the region may be kept spatially stationary. For detecting another set of x-rays, the region may be moved to a different location. During the detecting the other set of x-rays, the region may again be kept spatially stationary.

Contrary to conventional x-ray irradiations, where a punctiform x-ray source irradiates a planar detector and thus generates a radiation geometry that irradiates the object to be imaged in a planar fashion, a different radiation geometry is developed. A spatially stationary region of a detector is successively irradiated from different positions. The radiation geometry is therefore developed successively. For example, the x-rays that are emitted from the first position of the structure onto the region of the detector form the first partial irradiation, and the x-rays that are subsequently emitted from the second position onto the region of the detector form the second partial irradiation. The partial irradiations irradiate the object at a different point in each instance and thus develop a radiation geometry that irradiates the object in a planar fashion.

The individual positions form an at least one-dimensional structure (i.e., the individual positions are arranged along the at least one-dimensional structure).

A configuration of this type is advantageous in that there is greater freedom with respect to the structure of the source arrangement and with respect to the detector arrangement. Since the source arrangement is at least one-dimensional instead of punctiform, more favorable geometric configurations may be selected, where a shortage of space prevents the use of conventional x-ray configurations.

In one embodiment, the structure, from which the several partial irradiations are generated, may be two-dimensional. The region of the detector arrangement that is struck by the several partial irradiations may be punctiform so that the developing radiation geometry has an inverse conical form. In this case, the partial irradiations to be implemented successively are linear or one-dimensional. The dimensionality of the source arrangement (e.g., two-dimensional) and detector arrangement (e.g., punctiform) is precisely inverted in comparison with a conventional x-ray system.

In another embodiment, the structure, from which the x-rays for the several partial irradiations are directed at the region of the detector arrangement, is one-dimensional. The region of the detector arrangement that is struck by several partial irradiations has an elongated form with an extension in the longitudinal direction that is larger than an extension in the transverse direction. The region of the detector arrangement is arranged relative to the one-dimensional structure such that the longitudinal direction of the region is essentially at right angles to the direction of the one-dimensional structure.

The region may essentially be one-dimensional (e.g., using a detector array extending one-dimensionally with one line or a few lines of detector pixels) so that the developing radiation geometry is essentially tetrahedral. The partial irradiations, which are implemented successively with this geometry, are essentially fan-shaped or two-dimensional.

In the event that the region is not one-dimensional but instead two-dimensional and embodied in elongated form, the irradiations are conical with an elongated base surface.

Compared with a one-dimensional region, an elongated, two-dimensional region is advantageous in that fewer partial irradiations are needed in order to irradiate the object with adequate density in a planar fashion.

With these embodiments, both the source arrangement and also the detector are embodied in elongated form. In comparison with a two-dimensional embodiment of the source or of the detector, an imaging apparatus of this type may often be used if conventional imaging apparatuses may not be used because of space constraints.

In one embodiment of the source arrangement, an x-ray source with a positioning apparatus may be provided, such that x-rays may be emitted from different positions. The x-ray source may be positioned at the different positions with the positioning apparatus. An electron beam may be diverted by the positioning apparatus to different positions of a target, for example.

In another embodiment, the source arrangement may form several x-ray radiation sources that are positioned at different positions. This may be realized in a space-saving fashion, for example, with the aid of several carbon nanotube x-ray sources.

In addition to the first detector arrangement, the imaging apparatus may include a second detector arrangement that is separate from the first detector arrangement. Second detector arrangement x-rays may be directed at the second detector arrangement. The directing of the x-rays onto the second detector arrangement takes place similarly to the directing of the x-rays onto the first detector arrangement. A second radiation geometry that irradiates the object in a planar fashion is generated by directing the x-rays onto the second detector arrangement. The second radiation geometry includes a different spatial orientation from that of the first radiation geometry, so that the object may be irradiated from at least two different directions for stereoscopic imaging, for example. If a second source arrangement is also provided in addition to the second detector arrangement, the object may essentially be irradiated at the same time. This is also possible with just one source arrangement, if several x-ray sources are provided.

An evaluation unit determines an irradiation image from the recorded detector signals. The irradiation image, which images the object in a similar fashion to a conventional x-ray recording, may be shown to a user or stored.

In one embodiment, the source arrangement and the detector arrangement may be arranged so as to be rotatable about the object to be examined. By rotating the source arrangement and the detector arrangement, a plurality of radiation geometries, which are rotated counter to one another, developed similarly and may be generated with a different angle of rotation, respectively irradiate the object in a planar fashion.

Similarly to the reconstruction of a cone beam CT recording, the evaluation unit may be configured so as to determine a three-dimensional volume data set from the individual planar irradiations that are rotated counter to one another.

The evaluation unit may be configured so as to implement a resorting such that partial irradiations that belong to different radiation geometries are grouped together. A new radiation geometry is generated by the grouping of the partial irradiations. For example, a conical radiation geometry may be developed from partial irradiations that belong to different tetrahedral radiation geometries.

A radiation therapy device includes an imaging apparatus of this type, with the radiation therapy device including a beam exit, from which therapeutic radiation is directed onto a patient. The source arrangement is arranged at the beam exit, and the detector arrangement is arranged in the direction of the therapy beam behind the patient.

In another variant, the radiation therapy device may include a similar imaging apparatus, with the detector arrangement being arranged at the beam exit, and the source arrangement being arranged in the direction of the therapy beam behind the patient.

As a result of the imaging apparatus operating with a novel radiation geometry, the imaging apparatus may be arranged in a space-saving fashion and closely along the therapy beam. The radiation geometry may include a central axis that is tilted relative to the central axis of the therapy beam by less than 30°. In one embodiment, the central axis is tilted relative to the central axis of the therapy beam by less than 15°.

A method for generating an image of an object includes defining a target region and assigning beam bundles to the target region. The beam bundles are directed onto the target region in different partial irradiations from different positions. The different positions form an at least one-dimensional structure. The method also includes determining attenuation values that beam bundles experience when traversing the object. The total of the dimension of the structure and the dimension of the target region is greater than or equal to 2. The target region is left at the same location during the directing of the beam bundles in the case of different partial irradiations from the different positions onto the target region. The target region is aligned relative to the structure, such that a radiation geometry is developed by the different partial irradiations, the radiation geometry irradiating the object in a planar fashion.

The method may essentially reproduce the beam guidance that may be implemented with the imaging apparatus. The advantages and effects, which are described and explained in more detail for the imaging apparatus, therefore also apply accordingly to the method.

In one embodiment, the structure, from which the beam bundles are directed at the target region, is two-dimensional. The target region, at which the beam bundles are directed, is essentially punctiform so that the developing radiation geometry has an inverse conical form. The beam bundles are essentially linear.

In another embodiment, the structure, from which the beam bundles are directed at the target region, is one-dimensional. The target region, at which the beam bundles are directed, is embodied in elongated form with an extension in the longitudinal direction that is larger than an extension in the transverse direction. The target region is aligned relative to the one-dimensional structure such that the longitudinal direction of the target region is essentially at right angles to the one-dimensional structure. If the target region is essentially one-dimensional, a radiation geometry that is essentially tetrahedral develops.

An irradiation image may be generated from the determined attenuation values that the plurality of beams experience when traversing the object.

The target region and the different positions, from which the beam bundle is emitted onto the target region, may be rotated together so that different, similarly developed radiation geometries that are rotated relative to one another in a different direction may be generated by rotation, the radiation geometries irradiating the object in a planar fashion. In this case, attenuation values may be determined with the different radiation geometries, respectively, and a three-dimensional volume data set of the object is reconstructed therefrom.

During the reconstruction of the three-dimensional volume data set, a resorting of the partial irradiations may be implemented such that partial irradiations that belong to different radiation geometries are grouped together. A new radiation geometry is generated by the grouping. The radiation geometries rotated relative to one another may be tetrahedral in each instance, and may result in a new group of combined partial irradiations from different radiation geometries that nevertheless include a conical geometry. In this case, known reconstruction algorithms may be adapted from the cone beam computed tomography.

The method may be implemented by the object being a body to be irradiated using x-ray radiation and the beam bundles being x-rays that originate from a source arrangement for x-rays. The target region may be a region of a detector arrangement for x-rays.

In another embodiment, the method may be implemented as a virtual reconstruction method on a three-dimensional imaging data set. In this case, the object is a three-dimensional imaging data set (e.g., a computed tomogram). The beams bundles are virtual beam bundles that are applied by the three-dimensional imaging data set, and the target region is a virtual region, at which the beam bundles are directed. The attenuation values correspond to a calculated attenuation that would occur when the virtual beam bundles traverse the imaging data set. A digitally reconstructed irradiation image may be reconstructed from the three-dimensional imaging data set from the attenuation values. This embodiment is partially reminiscent of a conventional reconstruction of a digitally reconstructed radiograph (DRR) from a three-dimensional imaging data set, in that only the new beam geometry forms the basis of the reconstruction.

A computer program product includes a program code for implementing a reconstruction method of this type if the program code, stored in a non-transitory medium, is executed on a computer unit.

BRIEF DESCRIPTION OF THE DRAWINGS

FIG. 3 shows a representation of another radiation geometry for one embodiment of an x-ray apparatus, FIG. 4 shows a modification of the beam geometry shown in FIG. 3.

DETAILED DESCRIPTION OF THE DRAWINGS

Figure 1:
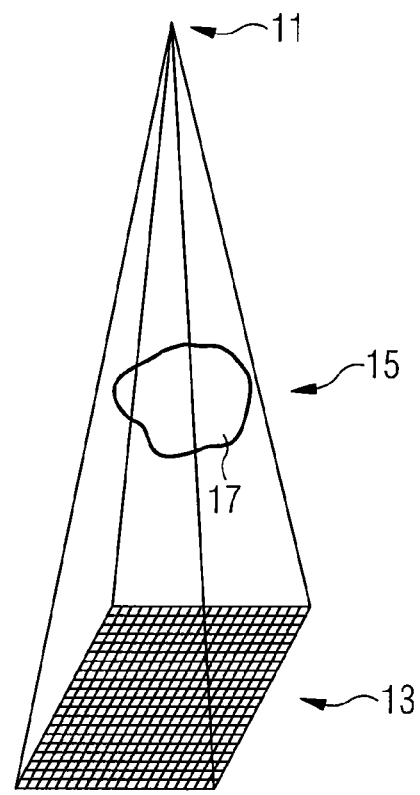
FIG. 1 shows a representation of the radiation geometry developed by an x-ray imaging system known in the prior art.

FIG. 1 shows a representation that illustrates the radiation geometry for an x-ray apparatus known in the prior art. X-rays 15 are emitted from an essentially punctiform source 11 onto a two-dimensional detector 13. "Two-dimensional" means that the individual detector elements are arranged along two dimensions. In this way, the x-rays 15 traverse an object 17 to be imaged in a planar fashion so that an irradiation recording may be produced. The geometry that the X-rays 15 generate corresponds to a cone.

Figure 2:
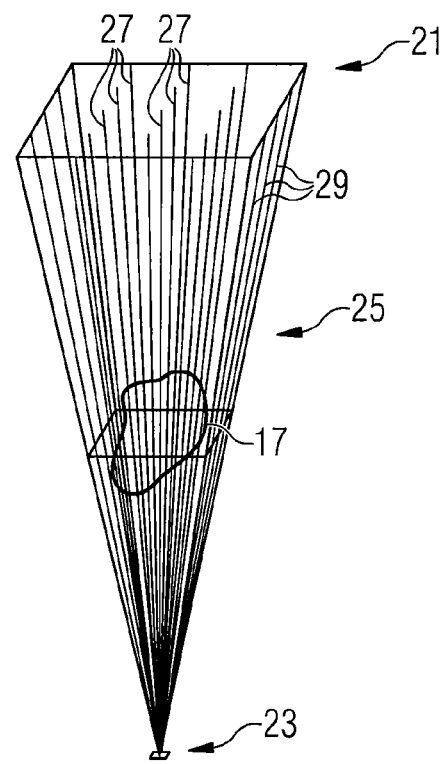
FIG. 2 shows a representation of a radiation geometry developed by one embodiment of an x-ray apparatus.

FIG. 2 shows a radiation geometry, as occurs in one embodiment of an x-ray apparatus. The x-ray apparatus includes a source arrangement 21 that is two-dimensional (e.g., the beams 25, which originate from the source arrangement 21, are emitted from positions 27 that are arranged along a planar region). The planar region shown in FIG. 2 is a planar rectangle. Other forms such as, for example, the arrangement of the positions along a spherical segment are also possible. The beams 25 are directed at an essentially punctiform detector 23. The developing radiation geometry exhibits an inverse conical shape.

The object 17 to be imaged is also irradiated in a planar fashion with the radiation geometry shown in FIG. 2. In the case of an irradiation with x-rays, the x-rays are successively directed into individual partial irradiations from the different positions 27 of the source arrangement 21 onto the punctiform detector 23. An irradiation image of the object may be produced from the temporally successive recorded detector signals.

This inverse conical geometry with a planar source arrangement 21 and punctiform detector 23 offers a reduced scatter radiation and thus an improved image quality. The imaging geometry corresponds to the regular imaging geometry with a punctiform source 11 and a planar detector 13 and generates images to which the user of conventional devices is accustomed. The high number of foci in the source arrangement 21 produces a high thermal load in the case of x-ray sources. This load may be reduced by a smaller spatial resolution in the source arrangement 21.

The resolution, which may also be reduced in the image plane as a result, may be compensated by an enlargement of the punctiform detector 23. This offers the use of a detector array that is extended in one or two dimensions (not shown here). Compared with conventional imaging in the conical geometry, the array may, however, be essentially smaller.

An imaging system with a completely inverse conical geometry may be mechanically combined with a device for radiation therapy, since the small punctiform detector 23 may be assembled adjacent to a beam exit without any problem. As a result, an "inline" geometry may be realized with a small angular error. A stereoscopic imaging may also be realized when using two detectors and/or sensors.

FIG. 3 shows a representation of a further radiation geometry, in which a one-dimensional source arrangement 31 and a one-dimensional detector arrangement 33 interact with one another. Beam bundles 35 are emitted from different positions 37, which are arranged along a one-dimensional structure (e.g., along a straight line).

The beam bundles 35 emitted from the different positions 37 into individual partial irradiations 37 are fan-shaped and strike the detector 33, the detector elements of which extend along a dimension. The detector 33, which is essentially configured one-dimensionally, is arranged such that the direction of the detector 33 is at right angles to the direction of the structure, along which the positions 37 are arranged, from which the individual partial irradiations 39 are produced. The radiation geometry, which is developed by a configuration of this type, exhibits a tetrahedral shape. The essentially one-dimensional source arrangement 31 and the essentially one-dimensional detector arrangement 33 are disposed at two opposite edges of the tetrahedron.

The presented radiation geometry provides for a two-dimensional imaging in a plane between the source arrangement 31 and the detector arrangement 33. The essentially one-dimensional geometry of the detector 33 and source 31 produces the option of a mechanically more compact structure. The partially inverse geometry reduces the scatter radiation onto the detector 31 and increases the image quality.

In comparison with a beam geometry with a completely inverse conical form, as shown in FIG. 2, the thermal load of a source arrangement 31 may be reduced for x-rays, since the load is not increased quadratically but instead only linearly.

FIG. 4 shows a modification of the configuration shown in FIG. 3. In this example, the positions 37, from which beams 35 are emitted and from which partial irradiations 39 are produced, are arranged along a one-dimensional structure. Contrary to the embodiment shown in FIG. 3, the structure is curved in a circular arc. The developing radiation geometry essentially corresponds to a tetrahedron, and a tetrahedron edge is slightly curved.

Figure 5:
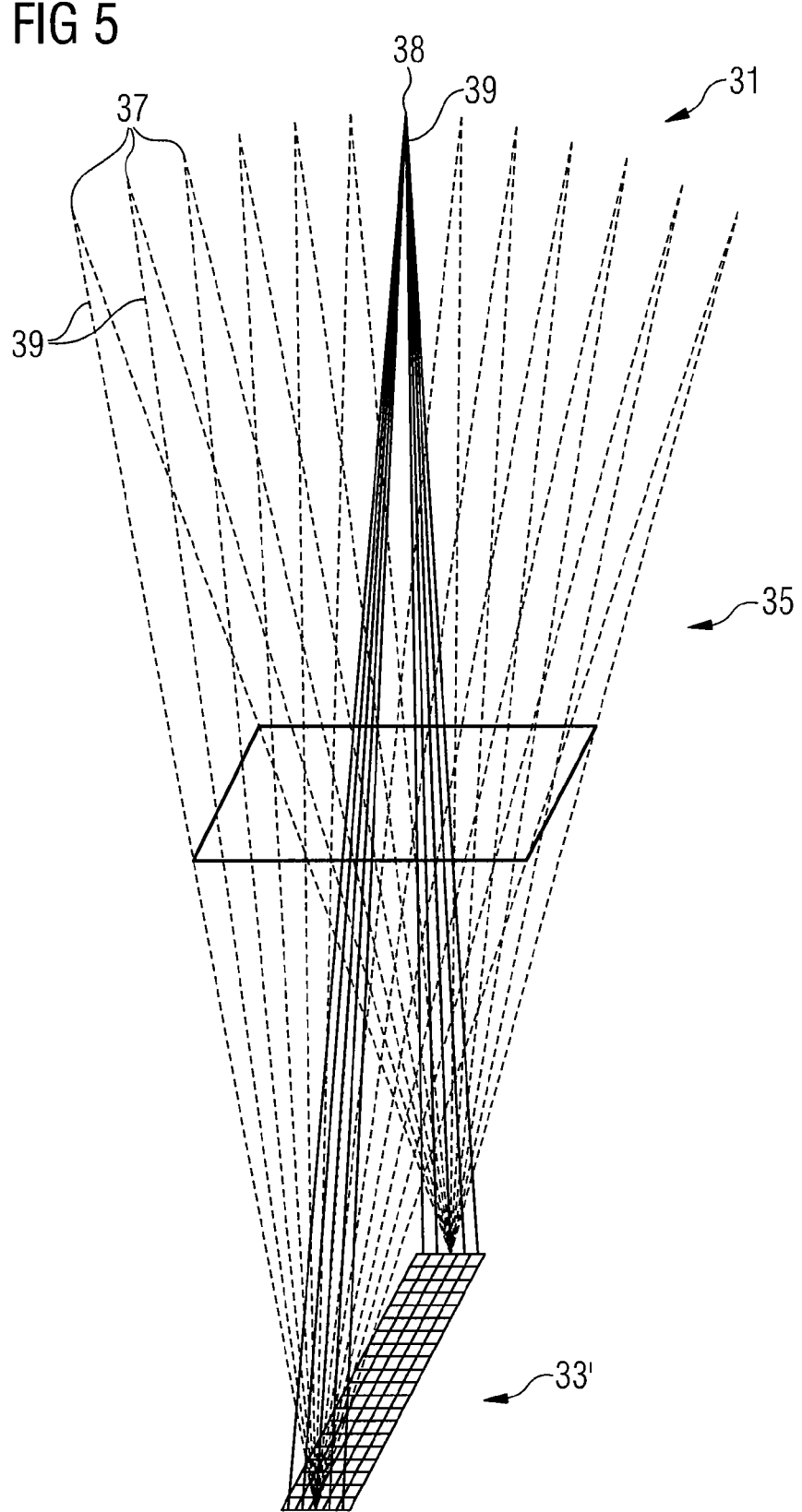
FIG. 5 shows a modification of the beam geometry shown in FIG. 4.

FIG. 5 shows a modification of the configuration shown in FIG. 4. In this example, the detector 33' is not one-dimensional, but instead includes detector elements that are arranged in a two-dimensional array. The array is elongated and has an extension in the longitudinal direction that is significantly larger than the extension in the transverse direction. The longitudinal direction of the array is arranged at right angles to the structure, from which the individual partial irradiations 39 are produced. The extension in one direction may be at least 5 times larger than in the other direction, for example. In another embodiment, the extension in one direction may be at least 10 times larger than in the other direction.

For the sake of clarity, the complete radiation path is only shown from one central position 38. The radiation path of a partial irradiation exhibits a conical shape with a base surface that corresponds to the elongated form of the detector arrangement 33'.

The embodiment shown in FIG. 5 is advantageous in that partial irradiations 39 are produced from, on the whole, fewer positions 37 along the one-dimensional structure, in order to irradiate the object (not shown here) in a planar fashion with the same resolution as with a configuration shown in FIG. 4.

To implement a source arrangement 31 of this type for x-rays, tubes with a deflected electron beam or x-ray tubes with individual discrete foci may be used, for example. Since the number of x-ray foci may be less in comparison with the number of pixels in two-dimensional detectors, a reduced resolution of the image would result in one direction in a configuration according to FIG. 4. This may be compensated by an elongated, two-dimensional detector and/or a two-dimensional detector array 33' being used instead of a one-dimensional detector 33 as in FIG. 4. The extension of the detector in the second dimension enables compensation of the lower resolution on the part of the x-ray source arrangement.

Figure 6:
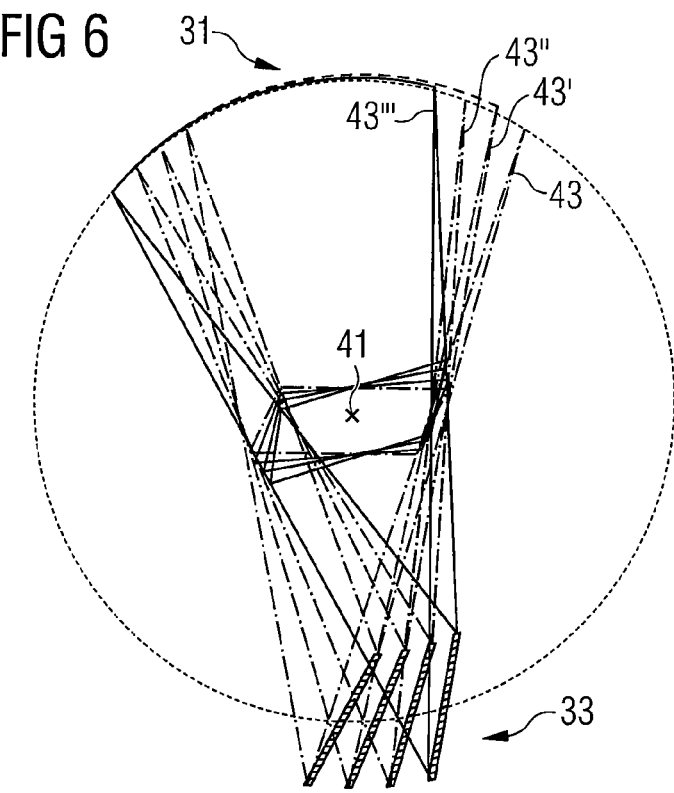
FIG. 6 shows a representation of the beam geometry according to FIG. 4.

FIG. 6 shows a representation of the radiation geometry shown in FIG. 3, with both the detector arrangement 33 and also the source arrangement 31 being arranged so as to be rotatable about a central point 41. In this way, the object (not shown here) may be illuminated in a planar fashion several times, with the individual planar irradiations and/or the associated radiation geometries 43-43''' being rotated relative to one another. An evaluation unit may generate a three-dimensional image, similar to a cone beam computer tomogram, from these individual partial irradiations which are rotated relative to one another.

A three-dimensional imaging of this type is advantageous in that soft part tissue may be shown differently. In order to be able to implement the reconstruction of layers, an irradiation of each layer is performed in different directions and different displacements. To a certain extent, an irradiation with partially missing beam directions is also adequate for a qualitatively somewhat poorer reconstruction. A rotating tetrahedral geometry enables sufficient irradiations to be generated in order to perform a reconstruction of the layers.

Figure 7:
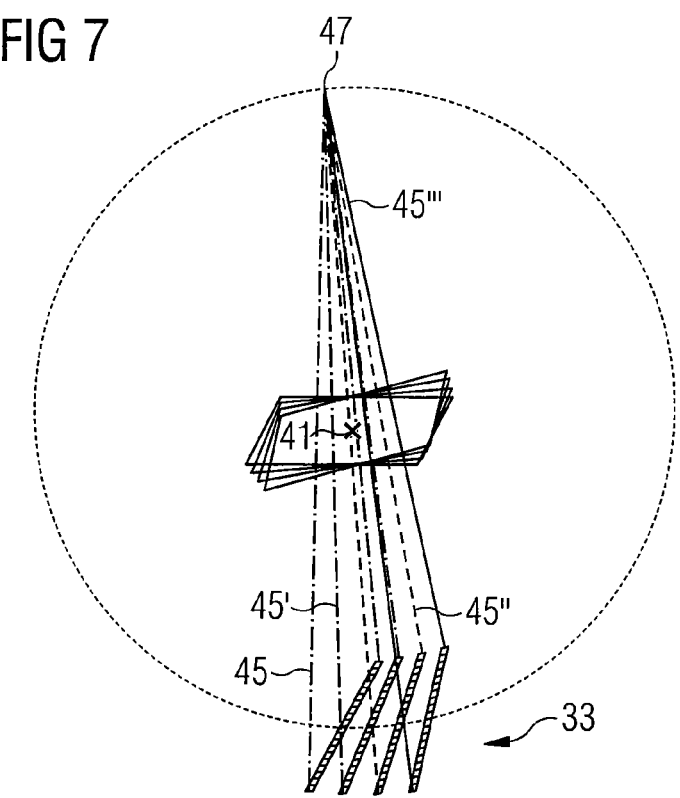
FIG. 7 shows a representation of resorting of individual partial irradiations.

With the evaluation, a resorting of individual partial irradiations may be implemented, as is shown in more detail with the aid of FIG. 7.

An individual partial irradiation 45-45''' is singled out in each instance from the four radiation geometries 43-43''' that are rotated relative to one another and shown in FIG. 6. Common to the singled-out partial irradiations 45-45''' is that the partial irradiations 45-45''' have been produced from the same spatial position 47. This may be achieved, for example, by the imaging apparatus being rotated to such a degree as corresponds with the distance of the individual positions of the source arrangement 31. Since the partial irradiations have, however, been produced in the case of a different rotational condition of the detector arrangement 33, if the singled out partial irradiations 45-45''' are combined to form a group, a planar irradiation of the object is produced with a radiation geometry taking the conical form.

Different partial irradiations 45-45''' are therefore combined to form a recording at different rotational angles and with different focus positions, the recording corresponding to a recording in the conical beam geometry.

Since algorithms for reconstructing a computer tomography from conical beam geometries perform a resorting of the beams, these two different resortings may be combined to form a single act.

If a resorting of this type is implemented, a three-dimensional image may be reconstructed by known reconstruction algorithms marginally modified for the cone beam computer tomography, since reconstruction algorithms of this type may relate to conical beam geometry. The reconstruction may be implemented, for example, using the Feldkamp algorithm.

Another possibility of representing soft tissue is the digital tomosynthesis (DTS). DTS images may be generated, for example, from adjacent recordings that have been made using a one-dimensional source and a one-dimensional detector.

In one embodiment, DTS images may be generated using a two-dimensionally extended detector 33', as shown in FIG. 5, for example. With a sufficiently high density of positions 37, from which x-rays 35 are emitted onto the two-dimensionally extended detector 33, each point of the image plane is not only drawn through by a beam and/or partial irradiation 39, but instead by beams with different directions. The combination of a one-dimensional source 31 with a multidimensional detector 33 having an alignment relative to one another according to FIG. 5 enables DTS images to be generated in the image plane. An application in the radiation therapy allows for rapid imaging in combination with an increased soft part contrast.

In another embodiment, DTS images may be generated using a two-dimensionally extended source arrangement 21 (as shown in FIG. 2), with a two-dimensionally extended detector. Points of the imaging plane are also irradiated from different directions, and this may be used for a correct 2D imaging in a restricted depth region.

Figure 8:
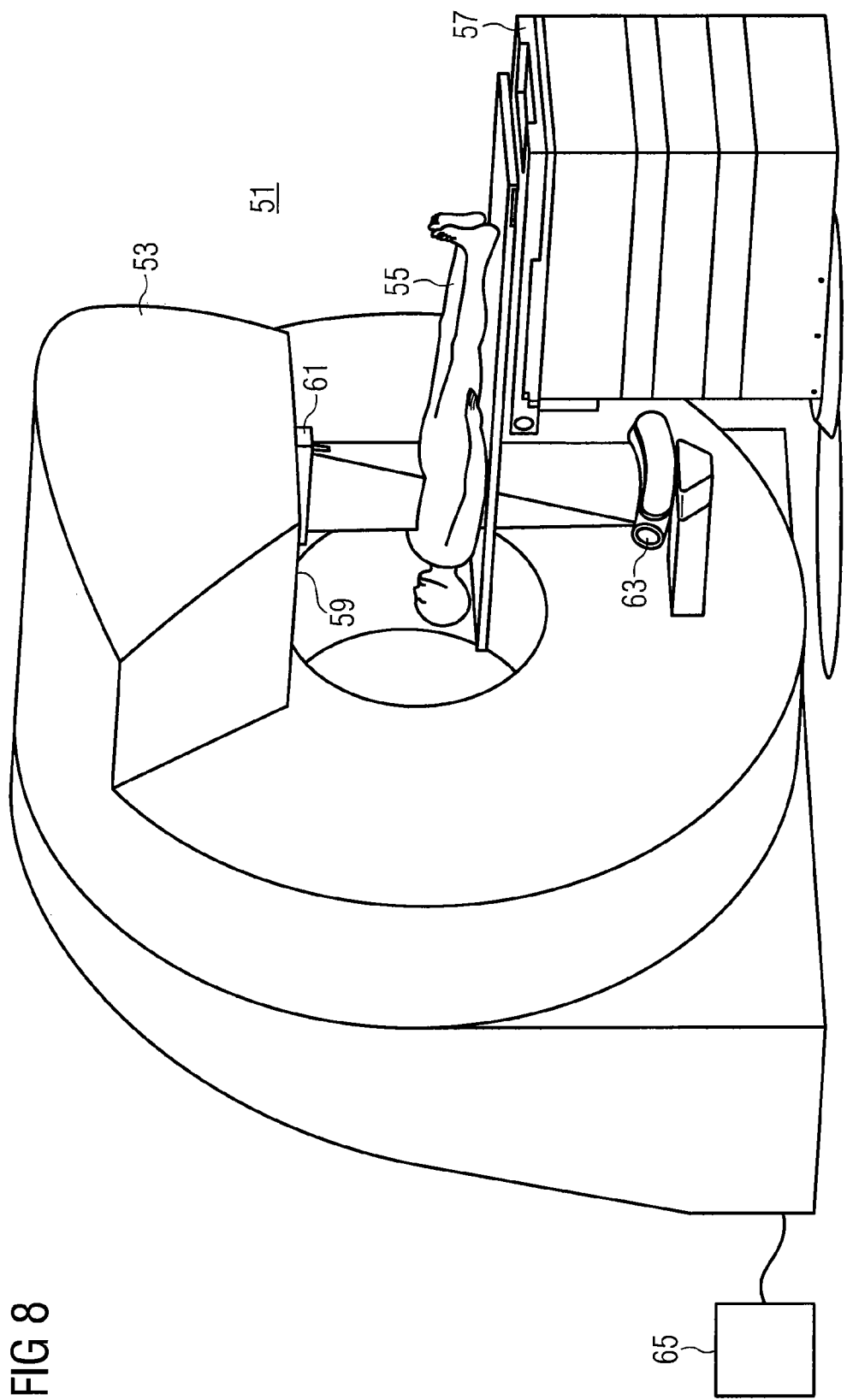
FIG. 8 shows one embodiment of a radiation therapy device.

FIG. 8 shows a perspective view of a radiation therapy device 51, in which an imaging system is integrated with a radiation geometry according to FIG. 4.

The radiation therapy device 51 includes a projecting arm 53, from which a therapy beam with therapeutic radiation may be directed onto a patient 55. The patient 55 is positioned in the radiation therapy device 51 by a patient couch 57. The radiation therapy device 51 has an L-shaped configuration as a result of the projecting arm 57. Other configurations of a radiation therapy device, in which embodiments of the imaging system may be used advantageously, are possible. The radiotherapy device includes a gantry that carries the projecting arm 53. The gantry may rotate to allow the radiation beam to be directed from different directions to the patient 55. The axis of rotation is parallel to the direction of the projecting arm and/or the patient body length axis.

A one-dimensional or elongated detector 61 is arranged in the direct vicinity of an exit point 59, from which the therapeutic treatment beam is directed onto the patient 51 by the projecting arm 53. In comparison with a two-dimensional detector, the one-dimensional and/or elongated detector 61 may be arranged closer to the exit point 61. An x-ray source 63 is provided in the therapy beam direction behind the patient, from which x-ray source x-rays are directed onto the detector in a fan-shaped and/or conical form with an elongated conical base surface. The detector 61 extends parallel to the axis of rotation of the gantry.

The detector arrangement 61 and the x-ray source 63 may be fixedly mounted on the gantry and permanently coupled to the gantry. Alternatively, the detector arrangement 61 and the x-ray source 63 may be mounted on the gantry using moveable arms, as a result of which greater freedom with respect to the positioning of the detector arrangement 61 and the x-ray source 63 results.

This configuration allows the patient 55 to be irradiated in a planar fashion in an imaging direction, the imaging direction having a very minimal angular offset in relation to the therapy beam and/or the central axis of the therapy beam. The imaging axis essentially corresponds with the axis of the therapy beam. The imaging essentially takes place in an "inline" geometry, the imaging plane running through the patient 51. This direction may be advantageous with respect to monitoring and checking the position of the tumor. Furthermore, the detector 61 or the source 63 may be prevented from being exposed to increased radiation load as a result of the therapy beam.

To evaluate the signals recorded by the detector 61, the radiation therapy device 51 includes a computer unit 65, with which the signals detected by the detector may be calculated to form an image of the patient 55 (e.g., to form an irradiation image), a three-dimensional volume data set or a digital tomosynthesis.

The imaging geometry of the imaging apparatus does not generate any images in the conical beam geometry, but instead in tetrahedral geometry. The images generated may be, as in the radiation therapy, generally compared with DRRs in order to determine the position of the patient 55 and, if necessary, to implement necessary position corrections.

Conventionally calculated DRRs are calculated in conical beam geometry and are therefore not directly suited to the comparison of images from the shown imaging system. It is therefore advantageous to calculate the comparison image from the 3D imaging data set, such that a radiation geometry corresponding to the imaging system (e.g., a tetrahedral geometry) is used.

Figure 12:
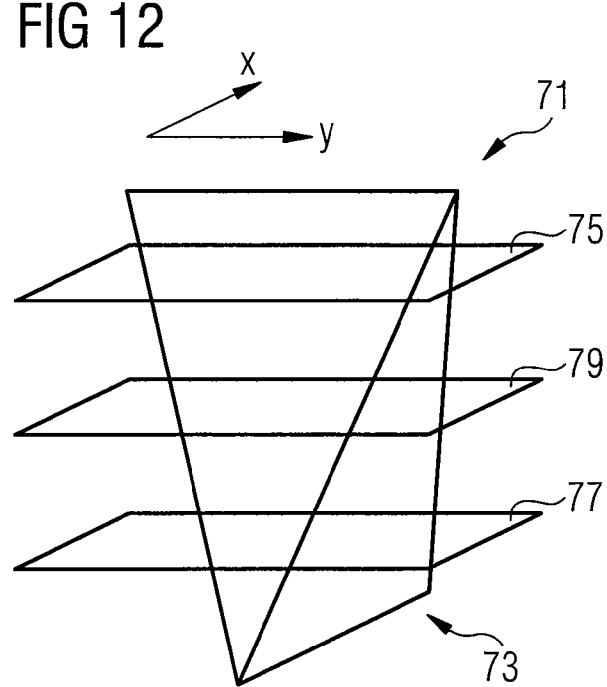
FIG. 12 shows a representation of the beam path for calculating DRRs using tetrahedron geometry.

FIG. 12 shows the radiation path, as may be laid by a 3D imaging data set, in order to calculate a DRR from a 3D imaging data set using tetrahedral geometry. An imaging plane 75 near to the source 71 is extended in the y-direction and is compressed in the x-direction, an imaging plane 77 near to the detector 73 is compressed in the y-direction and extended in the x-direction, while an imaging plane lying between the two has no compression and/or extension.

Figure 13:
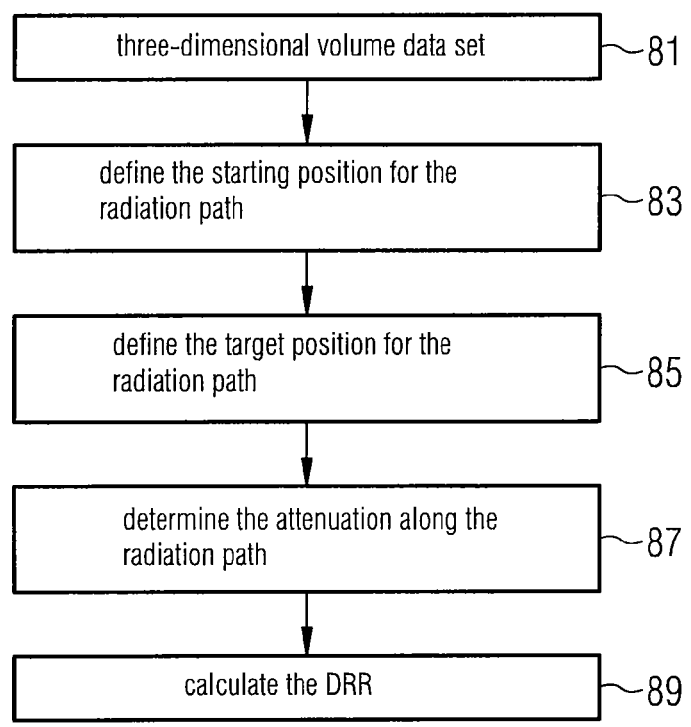
FIG. 13 shows a schematic representation of a method for calculating DRRs.

FIG. 13 shows a diagram of method acts, which are implemented during the calculation of a DRR from a three-dimensional volume data set. The volume data set is initially provided (acts 81). With the aid of a computer unit, positions, from which the radiation bundles are emitted with respect to the volume data set, along which the virtual attenuation is calculated with the aid of the information stored in the volume data set, are defined (act 83). Where the radiation bundles are emitted with respect to the volume data set is determined (act 85). The source and the target of the radiation bundle in the volume data set correspond to the geometry of the imaging apparatus, the irradiation images of which are to be compared with the DDR. Since the attenuation values have been calculated along the radiation bundle (act 87), the DDR is calculated (act 89) and shown to a user or stored in a computer unit.

Figure 9:
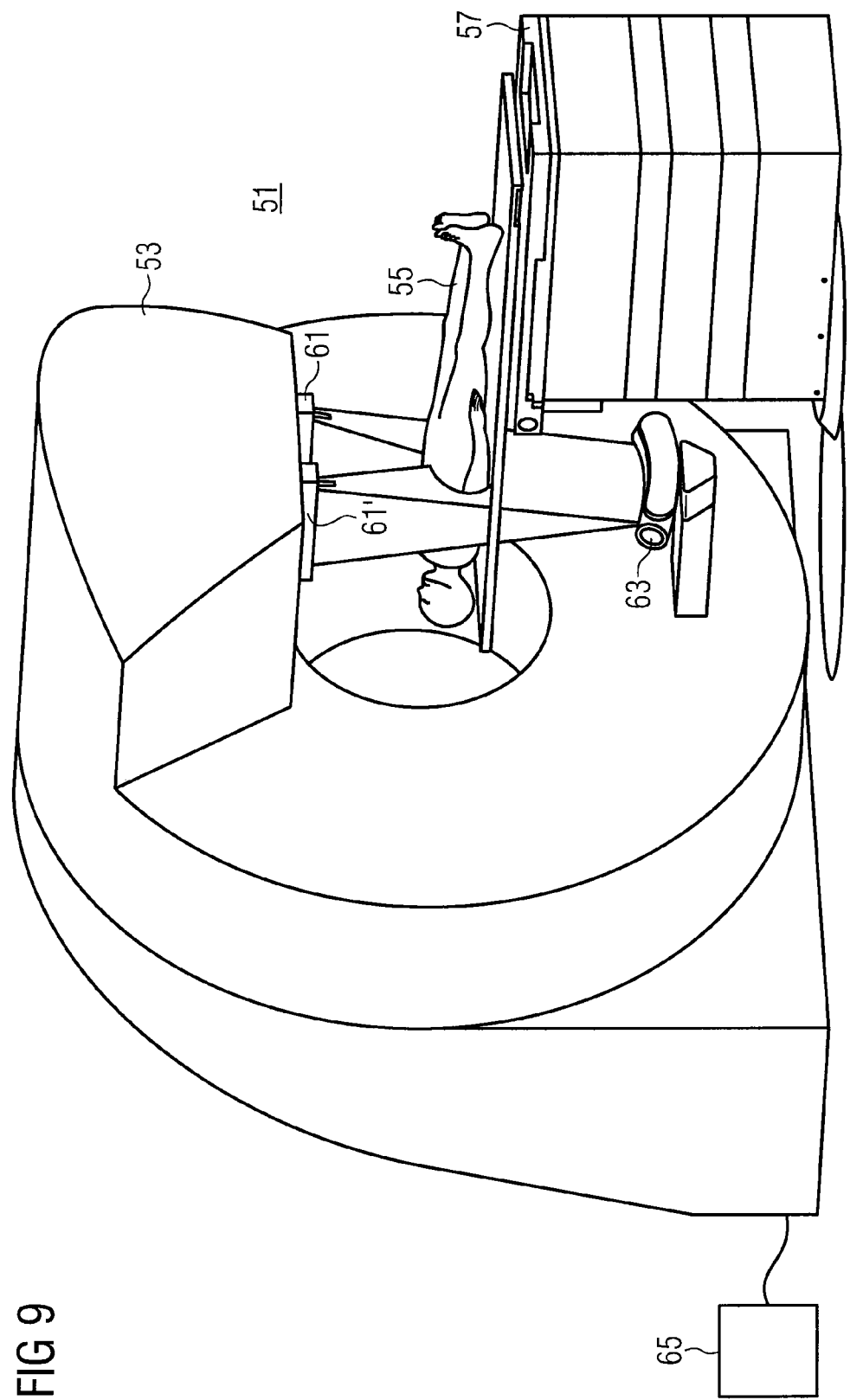
FIG. 9 shows one embodiment of a radiation therapy device with two detector arrangements.

FIG. 9 shows an embodiment of the radiation therapy device 51 shown in FIG. 8. Although the angular offset between the therapy beam and the imaging axis is very small, a further detector 61' may be disposed on the other side of the exit point on the projecting arm 53. As a result of the further detector 61' being configured in elongated form or one-dimensionally, only minimal additional costs result. With a system of this type, in which both detectors 61, 61' divide the x-ray source 63 arranged below the detectors, two images with opposite angular errors may be generated so that the angular error may be compensated.

Figure 10:
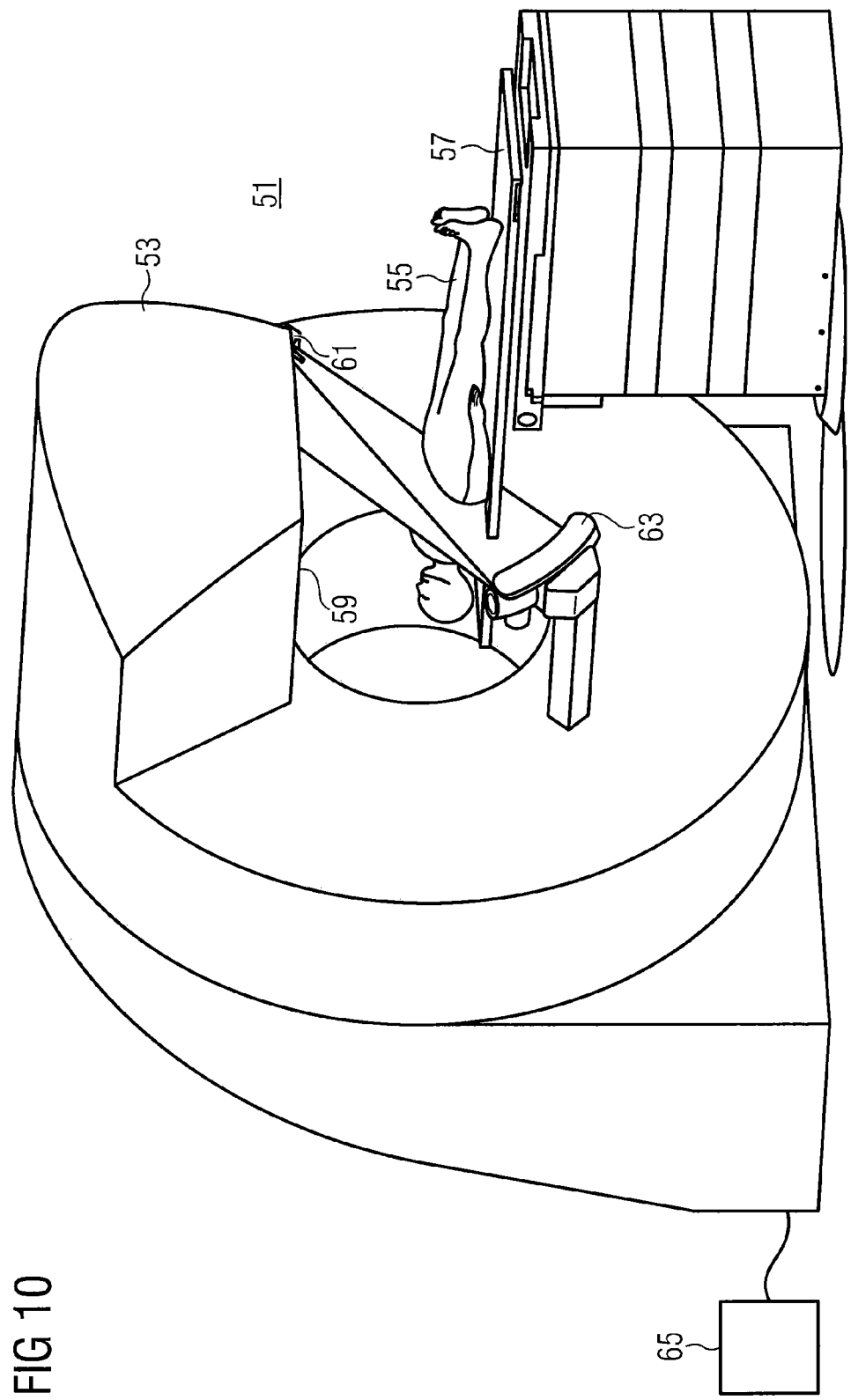
FIG. 10 shows one embodiment of a radiation therapy device with an angular offset between the imaging apparatus and the therapy beam.

FIG. 10 shows a radiation therapy device 51, in which the one-dimensional and/or elongated x-ray detector 61 is arranged with a larger angular offset relative to the therapy beam (i.e., the imaging takes place at a clearly different angle than the irradiation). This may be advantageous if the target volume and/or the position of the target volume is to be monitored along the therapy beam. The x-ray source 63 lies opposite the x-ray detector 61.

Figure 11:
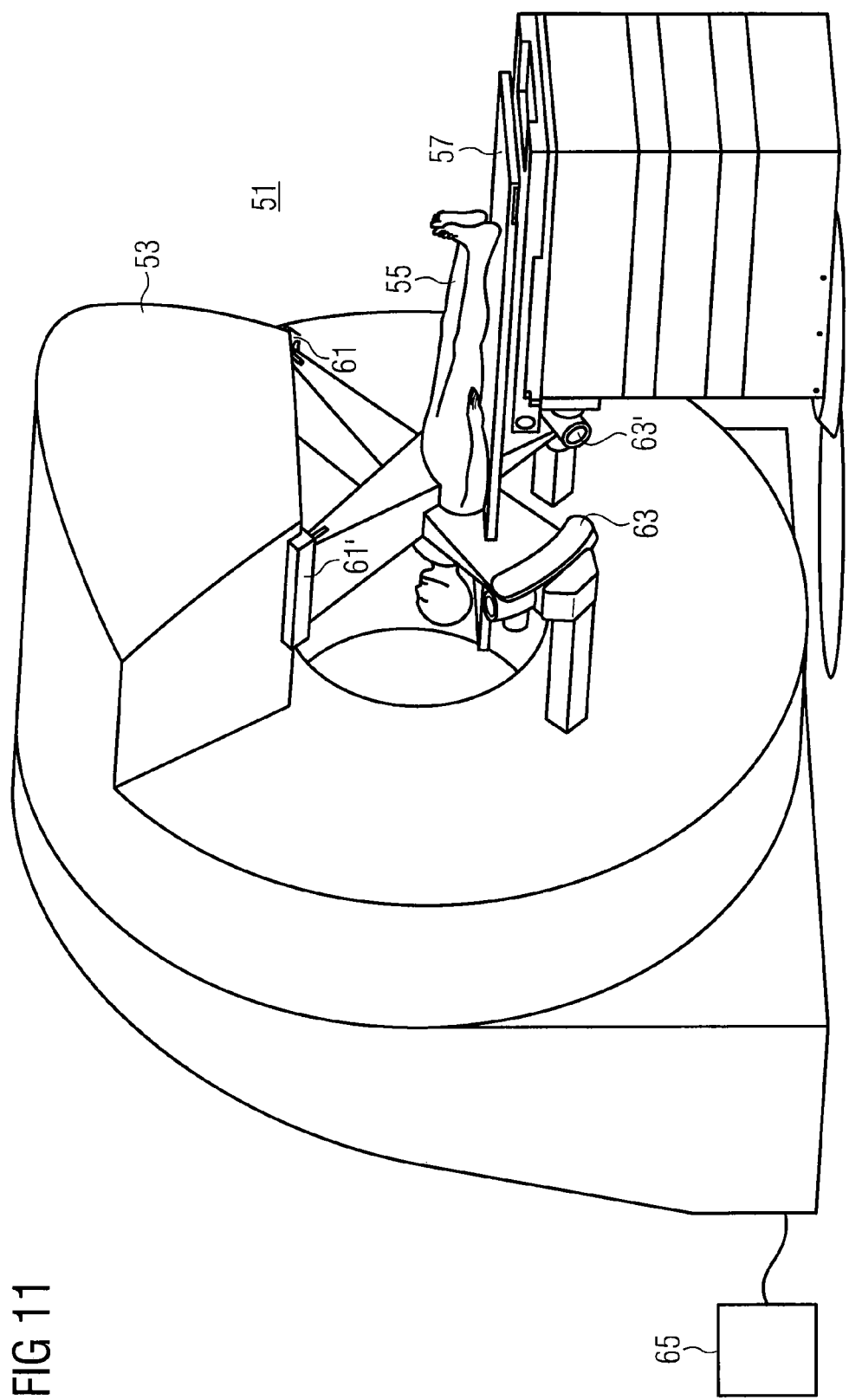
FIG. 11 shows one embodiment of a radiation therapy device with two detector arrangements and two source arrangements.

FIG. 11 shows an embodiment of the system shown in FIG. 10. In addition to the detector 61 and the x-ray source arrangement 63, a further detector 61' and a further x-ray source arrangement 63' are integrated in the system. In comparison with FIG. 10, the distance of the two detectors from one another and from the therapy beam is increased. Stereoscopic imaging may be possible with the embodiment shown in FIG. 11. To illuminate the two detectors, two separate x-ray source arrangements 63, 63' are provided in the example shown. Overall, the stereoscopic imaging enables the position of the target volume to be determined in the beam direction.

The x-ray sources 63, 63' shown in FIGS. 8 to FIG. 11 are in each case accommodated in a housing. The x-ray sources may each includes a plurality of punctiform foci that are arranged along the one-dimensional structure. "Jump focus" or "scanning-beam" x-ray sources may also be used.

An x-ray source, in which a moveable electron beam is deflected along a one-dimensional target and thus generates outgoing x-rays at different sites, may also be used. An x-ray source with a focus may also be arranged moveably and may be moved such that the radiation is generated from the different positions of the structure.

In FIGS. 8 to FIG. 11, the projecting arm 53 is arranged so as to be rotatable (i.e., the projecting arm 53 may rotate about the patient 55 so that the therapy beam may be deflected onto the patient 55 from different directions). The x-ray sources 63, 63' and the detectors 61, 61' may be rotated such that irradiations in the described radiation geometry are possible from different directions in each instance. The computer unit 65 may calculate a three-dimensional imaging data set of the patient 55 with the aid of the method described with FIG. 6 and FIG. 7.

Figure 14:
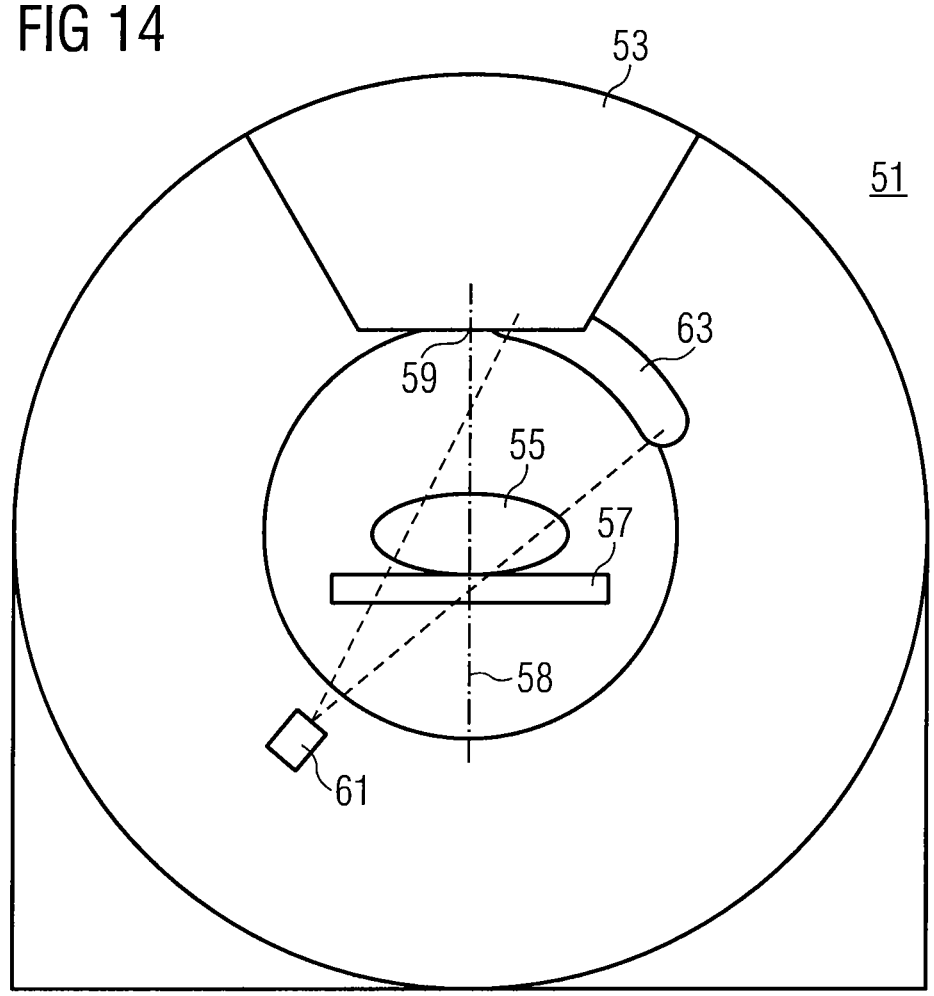
FIG. 14 shows a front view of one embodiment of a radiation therapy device.

FIG. 14 shows a schematic representation of a frontal view of one embodiment of the radiation therapy device 51. In the example shown in FIG. 14, the position of the x-ray source arrangement 63 and the detector 61 is flipped or exchanged compared with FIG. 10 (i.e., the detector 61 is located, when viewed in the beam direction of the therapy beam, behind the patient 55). In the frontal view, the exit point 59 and the therapy beam central axis 58 may also be seen more precisely.

The examples shown here are only embodiments of the invention. Other combinations of the features shown here are also conceivable. It is therefore possible to provide a radiation therapy device that includes an imaging apparatus with a two-dimensional source arrangement and a punctiform detector according to FIG. 2 or a two-dimensional source arrangement with a one or two-dimensional detector. A radiation therapy device with two imaging apparatuses of this type, which are arranged offset relative to one another for stereoscopy, for example, may also be provided.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An imaging apparatus for irradiating an object with x-rays, the imaging apparatus comprising:
    a source arrangement, from which x-rays are emittable from different positions, the different positions forming an at least one-dimensional structure;
    a detector arrangement for detecting x-rays originating from the source arrangement and emitted onto the detector arrangement, wherein an object to be irradiated is arrangeable between the source arrangement and the detector arrangement, so that x-rays attenuated by the object are recordable with the detector arrangement; and
    an evaluation apparatus for evaluating signals recorded by the detector arrangement,
    wherein a region of the detector arrangement is assigned to different positions of the at-least one-dimensional structure, from which x-rays are directed at the region in partial irradiations,
    wherein a total of the dimension of the at least one-dimensional structure and the dimension of the region is greater than or equal to 2, and
    wherein the region is aligned relative to the at-least one-dimensional structure, such that the partial irradiations, which are produced from the different positions of the at-least one-dimensional structure with respect to the region of the detector arrangement, produce a radiation geometry that irradiates the object in a planar fashion.

2. The imaging apparatus as claimed in claim 1, wherein the structure, from which the x-rays are emittable for the partial irradiations, is two-dimensional, and
    wherein the region of the detector arrangement, which is struck by the partial irradiations, is punctiform so that a developed radiation geometry has an inverse conical shape.

3. The imaging apparatus as claimed in claim 1, wherein the structure, from which the x-rays for the partial irradiations are directed at the region of the detector arrangement, is one-dimensional,
    wherein the region of the detector arrangement, which is struck by several of the partial irradiations, is configured in elongated form with an extension in the longitudinal direction that is larger than an extension in the transverse direction, and
    wherein the region of the detector arrangement is arranged relative to the one-dimensional structure, such that the longitudinal direction of the region is essentially at right angles to the one-dimensional structure.

4. The imaging apparatus as claimed in claim 3, wherein the region is essentially one-dimensional so that a developed radiation geometry has a tetrahedral form.

5. The imaging apparatus as claimed in claim 1, wherein the source arrangement comprises an x-ray source with a positioning apparatus, and wherein a focus of the x-ray source is positionable at the different positions of the source arrangement.

6. The imaging apparatus as claimed in claim 1, wherein the source arrangement comprises a plurality of x-ray sources that are positioned on the different positions of the source arrangement.

7. The imaging apparatus as claimed in claim 1, further comprising a second detector arrangement, to which the x-rays are directable,
    wherein a second radiation geometry is generatable by directing the x-rays onto the second detector arrangement, the second radiation geometry irradiating the object in a planar fashion, and
    wherein the second radiation geometry has a different spatial orientation than the first radiation geometry, so that the object is essentially simultaneously irradiatable from at least two different directions.

8. The imaging apparatus as claimed in claim 1, wherein the evaluation apparatus is configured to determine an irradiation image from the recorded signals.

9. The imaging apparatus as claimed in claim 1, wherein the source arrangement and the detector arrangement are rotatable, so that by rotating the source arrangement and the detector arrangement, a plurality of radiation geometries that are rotated counter to one another are generated with different rotational angles and irradiate the object in a planar fashion.

10. The imaging apparatus as claimed in claim 9, wherein the evaluation apparatus is configured to determine a three-dimensional volume data set from the recorded signals.

11. The imaging apparatus as claimed in claim 10, wherein the evaluation apparatus is configured to implement a resorting, such that partial irradiations, which belong to different radiation geometries, are grouped together so that a new radiation geometry is generated by the grouping.

12. A radiation therapy device comprising:
    a beam exit, from which a therapy beam is directable at a patient; and
    an imaging apparatus comprising:
        a source arrangement, from which x-rays are emittable from different positions, the different positions forming an at least one-dimensional structure;
        a detector arrangement for detecting x-rays originating from the source arrangement and emitted onto the detector arrangement, wherein an object to be irradiated is arrangeable between the source arrangement and the detector arrangement, so that x-rays attenuated by the object are recordable with the detector arrangement; and an evaluation apparatus for evaluating signals recorded by the detector arrangement, wherein a region of the detector arrangement is assigned to different positions of the at least one-dimensional structure, from which x-rays are directed at the region in partial irradiations, wherein a total of the dimension of the at least one-dimensional structure and the dimension of the region is greater than or equal to 2, and wherein the region is aligned relative to the at-least one-dimensional structure, such that the partial irradiations, which are produced from the different positions of the at-least one-dimensional structure with respect to the region of the detector arrangement, produce a radiation geometry that irradiates the object in a planar fashion.

13. The radiation therapy device as claimed in claim 12, wherein the source arrangement is arranged at the beam exit, and the detector arrangement is arranged in a direction of the therapy beam behind the patient.

14. The radiation therapy device as claimed in claim 12, wherein the detector arrangement is arranged at the beam exit, and the source arrangement is arranged in a direction of the therapy beam behind the patient.

15. The radiation therapy device as claimed in claim 12, wherein the radiation geometry developed between the source arrangement and the detector arrangement has a central axis, which is tilted by less than 30° relative to a central axis of the therapy beam.

16. A method for generating an image of an object, the method comprising:
defining a target region;
assigning beam bundles to the target region, the beam bundles being directed onto the target region in different partial irradiations from different positions, the different positions forming an at least one-dimensional structure; and
determining attenuation values that the beam bundles experience when traversing the object,
wherein a total of the dimension of the structure and the dimension of the target region is greater than or equal to 2,
wherein the target region remains at a same location during the directing of the beam bundles in the different partial irradiations from the different positions onto the target region, and
wherein the target region is aligned relative to the structure, such that a radiation geometry is developed by the different partial irradiations, the radiation geometry irradiating the object in a planar fashion.

17. The method as claimed in claim 16, wherein the structure, from which the beam bundles are directed at the target region, is two-dimensional, and
wherein the target region, at which the beam bundles are directed, is essentially punctiform so that the developed radiation geometry has an inverse conical form.

18. The method as claimed in claim 16, wherein the structure, from which the beam bundles are directed at the target region, is one-dimensional,
wherein the target region, at which the beam bundles are directed, is configured in elongated form with an extension in the longitudinal direction that is larger than an extension in the transverse direction, and
wherein the target region is arranged relative to the one-dimensional structure, such that the longitudinal direction of the target region is essentially at right angles to the one-dimensional structure.

19. The method as claimed in claim 18, wherein the target region is essentially one-dimensional so that the developed radiation geometry has a tetrahedral form.

20. The method as claimed in claim 16, further comprising generating an irradiation image from the determined attenuation values that the beam bundles experience when traversing the object.

21. The method as claimed in claim 16, further comprising rotating the target region and the different positions from which the beam bundles are emitted onto the target region together so that different, similarly developed radiation geometries, which are rotated relative to one another in a different direction, are operable to be generated by rotation, the radiation geometries irradiating the object in a planar fashion.

22. The method as claimed in claim 21, wherein determining the attenuation values comprises determining the attenuation values with the different radiation geometries and a three-dimensional volume data set of the object being reconstructed from the determined attenuation values.

23. The method as claimed in claim 22, further comprising resorting, during the reconstruction of the three-dimensional volume data set, the partial irradiations, such that partial irradiations, which belong to different radiation geometries, are grouped together to generate a new radiation geometry.

24. The method as claimed in claim 16, wherein the object is a body to be irradiated using x-ray radiation, and
wherein the beam bundles are x-rays that originate from a source arrangement for x-rays, and the target region is a region of a detector arrangement for x-rays.

25. The method as claimed in claim 16, wherein the object is a three-dimensional imaging data set,
wherein the beam bundles are virtual beam bundles that are laid by the three-dimensional imaging data set, and the target region is a virtual region, and
wherein a digitally reconstructed irradiation image is reconstructed from the three-dimensional imaging data set from the determined attenuation values.

26. A non-transitory computer program product having program codes, executable by a computer, for implementing a method for generating an image of a three-dimensional imaging data set, the method comprising:
defining, with a computer unit, a target region;
assigning beam bundles to the target region, the beam bundles being directed onto the target region in different partial irradiations from different positions, the different positions forming an at least one-dimensional structure; and
determining attenuation values that the beam bundles experience when traversing the object,
wherein a total of the dimension of the structure and the dimension of the target region is greater than or equal to 2,
wherein the target region remains at a same location during the directing of the beam bundles in the different partial irradiations from the different positions onto the target region,
wherein the target region is aligned relative to the structure, such that a radiation geometry is developed by the different partial irradiations, the radiation geometry irradiating the object in a planar fashion,
wherein the beam bundles are virtual beam bundles that are laid by the three-dimensional imaging data set, and the target region is a virtual region, and wherein a digitally reconstructed irradiation image is reconstructed from the three-dimensional imaging data set from the determined attenuation values.

* * * * *